(12) United States Patent
Mouradian et al.

(10) Patent No.: US 7,395,104 B2
(45) Date of Patent: Jul. 1, 2008

(54) METHODS AND DEVICES FOR NON-INVASIVELY MEASURING QUANTITATIVE INFORMATION OF SUBSTANCES IN LIVING ORGANISMS

(75) Inventors: Vahram Mouradian, Plano, TX (US); Valeri Armenakyan, Plano, TX (US); Maksim Malkin, Simpheropol (UA); Gagik Farmanyan, Plano, TX (US); Minas Hambardzumyan, Plano, TX (US)

(73) Assignee: Calisto Medical, Inc., Plano, TX (US)

( * ) Notice: Subject to any disclaimer, the term of this patent is extended or adjusted under 35 U.S.C. 154(b) by 185 days.

(21) Appl. No.: 11/074,283

(22) Filed: Mar. 6, 2005

(65) Prior Publication Data

US 2005/0197555 A1 Sep. 8, 2005

Related U.S. Application Data

(60) Provisional application No. 60/550,913, filed on Mar. 6, 2004.

(51) Int. Cl.
*A61B 5/05* (2006.01)
*A61B 5/00* (2006.01)

(52) U.S. Cl. .................. 600/347; 600/345; 600/365

(58) Field of Classification Search ................. 600/309, 600/345–366
See application file for complete search history.

(56) References Cited

U.S. PATENT DOCUMENTS

| | | | |
|---|---|---|---|
| 3,316,896 A | 5/1967 | Thomasset | |
| 4,016,870 A | 4/1977 | Lock | |
| 4,317,817 A | 3/1982 | Blohm | |
| 4,392,933 A | 7/1983 | Nakamura et al. | |
| 4,408,617 A | 10/1983 | Auguste | |
| 4,431,004 A | 2/1984 | Bessman et al. | |
| 4,436,094 A | 3/1984 | Cerami | |
| 4,557,271 A | 12/1985 | Stoller et al. | |
| 4,655,225 A | 4/1987 | Dahne et al. | |
| 4,714,080 A | 12/1987 | Edgar, Jr. et al. | |
| 4,882,492 A | 11/1989 | Schlager | |
| 4,883,953 A | 11/1989 | Koashi et al. | |
| 4,897,162 A | 1/1990 | Lewandowski et al. | |
| 4,911,175 A | 3/1990 | Shizgal | |
| 4,947,862 A | 8/1990 | Kelly | |
| 5,028,787 A | 7/1991 | Rosenthal et al. | |
| 5,036,861 A | 8/1991 | Sembrowich et al. | |
| 5,050,612 A | 9/1991 | Matsumura | |

(Continued)

FOREIGN PATENT DOCUMENTS

WO WO 2003/062214 A1 5/2002

(Continued)

*Primary Examiner*—Charles A. Marmor, II
*Assistant Examiner*—Navin Natnithithadha
(74) *Attorney, Agent, or Firm*—Carr LLP (57) ABSTRACT

Disclosed are systems and methods of determining the amount of a substance in a living organism. In one embodiment, the method comprises: applying an electrical signature signal to the living organism, wherein the electrical signature signal corresponds to a predetermined amount of the substance; measuring the response of the living organism to the applied signature signal; and determining whether an elevated response has resulted from applying the electrical signature signal, if so, then determining the amount of the substance in the living organism from the predetermined amount of the substance.

6 Claims, 10 Drawing Sheets

U.S. PATENT DOCUMENTS

| | | | |
|---|---|---|---|
| 5,063,937 A | 11/1991 | Ezenwa | |
| 5,070,874 A | 12/1991 | Barnes et al. | |
| 5,077,476 A | 12/1991 | Rosenthal | |
| 5,086,229 A | 2/1992 | Rosenthal et al. | |
| 5,115,133 A | 5/1992 | Knudson | |
| 5,131,401 A | 7/1992 | Westenskow et al. | |
| 5,139,023 A | 8/1992 | Stanley et al. | |
| 5,146,091 A | 9/1992 | Knudson | |
| 5,163,439 A | 11/1992 | Dardik | |
| 5,170,199 A | 12/1992 | Nakai | |
| 5,197,951 A | 3/1993 | Mahurkar | |
| 5,222,495 A | 6/1993 | Clarke et al. | |
| 5,222,496 A | 6/1993 | Clarke et al. | |
| 5,267,152 A | 11/1993 | Yang et al. | |
| 5,322,063 A | 6/1994 | Allen et al. | |
| 5,339,827 A | 8/1994 | Masopust | |
| 5,360,004 A | 11/1994 | Purdy et al. | |
| 5,368,028 A | 11/1994 | Palti | |
| 5,372,141 A | 12/1994 | Gallup | |
| 5,379,764 A | 1/1995 | Barnes et al. | |
| 5,433,197 A | 7/1995 | Stark | |
| 5,458,140 A * | 10/1995 | Eppstein et al. | 600/573 |
| 5,562,596 A * | 10/1996 | Pincus et al. | 600/17 |
| 5,568,049 A | 10/1996 | Bucholtz | |
| 5,579,782 A | 12/1996 | Masuo | |
| 5,590,650 A | 1/1997 | Genova | |
| 5,720,296 A | 2/1998 | Cha | |
| 5,722,397 A * | 3/1998 | Eppstein | 600/345 |
| 5,725,480 A | 3/1998 | Oosta et al. | |
| 5,752,512 A | 5/1998 | Gozani | |
| 5,769,793 A * | 6/1998 | Pincus et al. | 600/515 |
| 5,817,031 A | 10/1998 | Masuo | |
| 5,830,140 A | 11/1998 | Dillinger et al. | |
| 5,846,189 A * | 12/1998 | Pincus | 600/301 |
| 5,890,489 A | 4/1999 | Elden | |
| 5,894,939 A | 4/1999 | Frankel | |
| 6,016,445 A | 1/2000 | Baura | |
| 6,044,285 A | 3/2000 | Chaiken et al. | |
| 6,120,460 A | 9/2000 | Abreu | |
| 6,246,893 B1 | 6/2001 | Gobeli | |
| 6,261,236 B1 | 7/2001 | Grimblatov | |
| 6,266,774 B1 | 7/2001 | Sampath et al. | |
| 6,280,381 B1 | 8/2001 | Malin et al. | |
| 6,312,393 B1 | 11/2001 | Abreu | |
| 6,328,694 B1 | 12/2001 | Michaeli | |
| 6,377,828 B1 | 4/2002 | Chaiken et al. | |
| 6,400,983 B1 | 6/2002 | Cha | |
| 6,424,847 B1 * | 7/2002 | Mastrototaro et al. | 600/316 |
| 6,456,865 B2 | 9/2002 | Samson | |
| 6,490,481 B1 | 12/2002 | Komatsu | |
| 6,517,482 B1 | 2/2003 | Elden et al. | |
| 6,522,903 B1 | 2/2003 | Berman et al. | |
| 6,544,193 B2 | 4/2003 | Abreu | |
| 6,558,320 B1 | 5/2003 | Causey, III et al. | |
| 6,565,509 B1 | 5/2003 | Plante et al. | |
| 6,594,521 B2 | 7/2003 | Tucker | |
| 6,599,253 B1 | 7/2003 | Baum et al. | |
| 6,631,282 B2 | 10/2003 | Rule et al. | |
| 6,702,743 B2 | 3/2004 | Michaeli | |
| RE38,492 E * | 4/2004 | Diab et al. | 600/364 |
| 6,760,617 B2 | 7/2004 | Ward et al. | |
| 6,841,389 B2 | 1/2005 | Novikov et al. | |
| 6,865,407 B2 | 3/2005 | Kimball et al. | |
| 6,866,675 B2 | 3/2005 | Perez et al. | |
| 6,954,662 B2 | 10/2005 | Freger et al. | |
| 6,990,422 B2 | 1/2006 | Laletin et al. | |
| 6,996,428 B2 | 2/2006 | Kislov et al. | |
| 6,999,808 B2 | 2/2006 | Gobeli et al. | |
| 7,016,021 B2 | 3/2006 | Nakajima et al. | |
| 7,016,713 B2 | 3/2006 | Gardner et al. | |
| 7,027,848 B2 | 4/2006 | Robinson et al. | |
| 7,039,446 B2 | 5/2006 | Ruchti et al. | |
| 7,039,447 B2 | 5/2006 | Berman et al. | |
| 7,041,063 B2 | 5/2006 | Abreu | |
| 7,050,847 B2 | 5/2006 | Ollmar et al. | |
| 2002/0138099 A1 | 9/2002 | Markin et al. | |
| 2003/0009111 A1 | 1/2003 | Cory et al. | |
| 2003/0045809 A1 | 3/2003 | Kanevsky | |
| 2003/0220581 A1 | 11/2003 | Ollmar et al. | |
| 2004/0133081 A1 | 7/2004 | Teller et al. | |
| 2004/0133121 A1 | 7/2004 | Ohkura | |
| 2005/0197592 A1 | 9/2005 | Kanevsky | |
| 2005/0238693 A1 | 10/2005 | Whyte | |

FOREIGN PATENT DOCUMENTS

| | | | |
|---|---|---|---|
| WO | WO 2003/017834 A1 | 3/2003 | |

* cited by examiner

Fig. 6b

METHODS AND DEVICES FOR NON-INVASIVELY MEASURING QUANTITATIVE INFORMATION OF SUBSTANCES IN LIVING ORGANISMS

CROSS REFERENCE TO RELATED APPLICATIONS

This application claims the benefit of the filing date of U.S. provisional patent application Ser. No. 60/550,913, entitled "Methods And Devices For Non-Invasively Measuring Quantitative Information Of Substances In Living Organisms," filed on Mar. 6, 2004, the disclosure of which is incorporated herein by reference.

TECHNICAL FIELD

The invention relates in general to medical measuring devices and in particular to methods and devices for non-invasively measuring quantitative information of substances in living organisms.

BACKGROUND INFORMATION

The living organism and its functioning systems are sources of extremely weak electromagnetic oscillations in a broad spectrum of frequencies. Several holistic therapeutic processes take advantage of such principles. These therapeutic processes utilize specific ultra fine oscillation information and are generally known as "bioresonance therapy."

The term bioresonance therapy ("BRT") was coined in 1987 by the Brugemann Institute for "therapy using the patient's own electromagnetic oscillations." Such principles can be traced to the physician Dr. F. Morrell, who presented the use of his idea for the first time in 1977. Dr. Morrell's postulated that all disease and their pre-conditions are accompanied or caused by electromagnetic oscillations. According to Dr. Morrell's postulations, there is no pathological phenomenon without the presence of pathological oscillations in or around the body.

Pathological electromagnetic oscillations are active alongside the healthy oscillations in the body of every patient. Because the patent's own oscillations or signals are electromagnetic in nature, they can be detected by using electrodes and electromagnetic measurement devices. Using what is known as a separator, the harmonious oscillations, which are virtually identical in all humans, may be filtered out through a filter. Interfering frequencies, which may be caused by pathogens, are not captured by the filter. Thus, the separator only resonates with harmonious frequencies. In this way, it is possible to separate harmonious and disharmonious frequencies.

Diabetes is a life threatening disease which affects an estimated 20 million Americans, out of whom 50% are not aware of having it. The latest statistical estimates indicate there are approximately 125 million people diagnosed with diabetes worldwide, and that number is expected to rise 220+million by the year 2010. Early detection of diabetes is manageable allowing those affected to live longer and healthier lives. Blood glucose level monitoring and tracking provides valuable information to help control patients with diabetes. Diabetic people who using insulin regularly need to check the glucose level three or more times per day. This process of monitoring the glucose level allows doctors to have prompt and primary information in detecting the cure for disease.

During 1970's monitoring glucose level instruments were invented which based on chemical test strips which could react with drawn blood. Today, there are sophisticated electronic devices which are used to determine blood glucose levels; however, these devices still use invasive techniques to draw a sample of blood from the patient. However such techniques are invasive, inconvenient, and sometimes painful. Rather than use invasive techniques, such as blood tests, it would be desirable to use electromagnetic oscillations to determine the amounts of certain substances, such a blood glucose, within a living organism. Additionally, it would also be useful to use oscillations of various substances to determine the levels of any substance in a living organism.

What is needed, therefore, is a method and/or apparatus which can non-invasively test for substances, such as glucose levels in blood or the body in general by using electromagnetic oscillations.

SUMMARY

The previously mentioned needs are fulfilled with various embodiments of the present invention. Accordingly, in one embodiment, a method and system is provided for non-invasively measuring a level of a substance level in a living organism, the method comprises: measuring the electrical potential between points on different meridians of vegetative system, or between different points on the skin of the organism; storing the measured value as reference point; applying a plurality of low current electrical signals, where each signal corresponds to a previously extracted electrical signal derived from a known concentration of the substance to determine a maximum difference between the reference point and the responses to the electrical signals, then determining the amount of the substance in the living organism by using the maximum difference and previously determined table to correlate the amount of the substance with the maximum difference.

In another aspect, there is disclosed a method of determining a substance in a living organism, the method comprising: applying an electrical signature signal to the living organism, wherein the electrical signature signal corresponds to a predetermined amount of the substance; measuring the response of the living organism to the applied signature signal; and determining whether an elevated response has resulted from applying the electrical signature, if so, then determining the amount of the substance in the living organism from the predetermined amount of the substance.

In another aspect, the detection of the "body response" is based on the monitoring of the level of convergence of sequentially generated curves of conductivity change versus time for the same substance signature wave applied to the body between two points on the skin.

In another aspect, there is a process for the matching of self-oscillation frequencies of different concentrations of glucose molecules in the human blood with similar frequencies of pre-known concentrations of glucose in reference solutions. As a result of such a resonance or "GlucoResonance", the electrical potential between two predefined acupuncture points ("aculevel") on a human body changes significantly. This change represents the difference between the measured aculevel with and without GlucoResonance.

One aspect uses an internal database of self-oscillation frequencies extracted from hundreds of biological solutions with different levels of glucose, covering the range of blood glucose levels from 10 mg/dl to 600 mg/dl. In order to test for glucose in the blood, a low-current electrical signal for every entry in the reference database may be applied to a patient at predetermined points on the skin or acupuncture points. These electrical signals are applied at points where the electrical potential has been previously measured to establish a calibration aculevel. Then the measured aculevel for every data point is compared with the calibration aculevel. A large disturbance/change between these values suggests the blood glucose level in the patient.

In other aspects, there is disclosed an apparatus for measuring a substance in a living organism, the apparatus may comprise: a processor means; at least two electrode means for applying and receiving signals, an impedance measuring means for determining the impedance between the at least two electrode means; a memory means for storing a database of electrical signature signals, wherein each electrical signature signal corresponds to different amounts of a substance; and a means for applying the electrical signature signals to the at least two electrode means.

These and other features, and advantages, will be more clearly understood from the following detailed description taken in conjunction with the accompanying drawings. It is important to note the drawings are not intended to represent the only form of the invention.

BRIEF DESCRIPTION OF THE DRAWINGS

FIG. 3b is a continuation of the process illustrated in FIG. 3a.

FIG. 6b is an exploded perspective view of the portable device illustrated in FIG. 6a.

DETAILED DESCRIPTION OF THE INVENTION

It is understood, however, that the following disclosure provides many different embodiments, or examples, for implementing different features of the invention. Specific examples of components, signals, messages, protocols, and arrangements are described below to simplify the present disclosure. These are, of course, merely examples and are not intended to limit the invention from that described in the claims. Well-known elements are presented without detailed description in order not to obscure the present invention in unnecessary detail. For the most part, details unnecessary to obtain a complete understanding of the present invention have been omitted in as much as such details are within the skills of persons of ordinary skill in the relevant art. Details regarding control circuitry or mechanisms described herein are omitted; as such control circuits are within the skills of persons of ordinary skill in the relevant art.

Acupuncture points are well known in Chinese medicine. In the 1950's, Dr. Reinhard Voll studied acupuncture and learned that the body has about 2000 points on the skin which follow twenty lines called meridians. According to Chinese traditional medicine, meridians are channels of energy and that energy movement is called Qi. Western studies have also shown that acupuncture points may be found by mapping skin electrical resistances. Thus, acupuncture points are specific superficial anatomic locations where the skin on or over these points is lower in electrical resistance than the surround skin, making acupuncture points strategic conductors of electromagnetic signals in the body. Some studies have shown that acupuncture point resistance is approximately half that of the surrounding skin (or conductance is twice as higher). It is possible, therefore, to measure the galvanic skin or other paths' resistance or conductance at the acupuncture points to determine the resonance point of self oscillating frequency of the organism. In this case the human body is becoming the main detector of resonance point, while the conductance between any two different points on the body can be a secondary 'sensor' of the body reaction to the resonance event.

As discussed previously, in certain methods of therapy, disharmonious frequencies (e.g., the signature frequency of certain pathogens) may be filtered out and inverted. These inverted frequencies as well as harmonious oscillations from the separator may be fed back to the patient using an electrode. The patient's own electromagnetic field reacts to the therapy signals and in turn enters a modified pattern into the measurement devices and separator. This process may be repeated and thus the pathological signals in the body are consequently reduced and finally extinguished. It has been shown that eliminating the pathological signals from the body has a beneficial therapeutic effect.

One aspect of the present invention recognizes that certain substances, such as glucose also have a particular electromagnetic oscillation or frequency. For purposes of this application, a "substance" is matter of a particular or definite chemical composition, such as glucose. The oscillations associated with a particular substance may change as the amount of the substance changes within an organism. Thus, various aspects of the present invention use electromagnetic oscillations to determine the substance concentration, such a blood glucose, within a living organism.

As previously discussed, every substance also has its own magnetic "self" frequency oscillation. When the frequency of a reagent is introduced into the organism through an electrode, the frequency of the reagent interacts with the frequency of the organism and creates a change in amplitude of the frequency. The response or change in amplitude or "excitation" of the signal can be detected and measured. Thus, it is possible to determine which signal frequencies produces the greatest excitation when compared to the reference point (the reference point can be also a first conductance/resistance measurement applying the same reagent signature). When comparing a plurality of frequencies (each frequency corresponds to a known level of the substance), the frequency that produces the greatest excitation is the frequency that corresponds to the level of the substance in the organism.

Thus, for every reference correlation in a reference database, a low-current electrical signal having a particular frequency may be introduced into the organism, which is applied at acupressure points or any other points on the human body where the electrical potential has been previously measured. This process may be repeated for every correlation in the reference database until a match (e.g. the signal that produces the greatest excitation) is found.

Figure 1A:
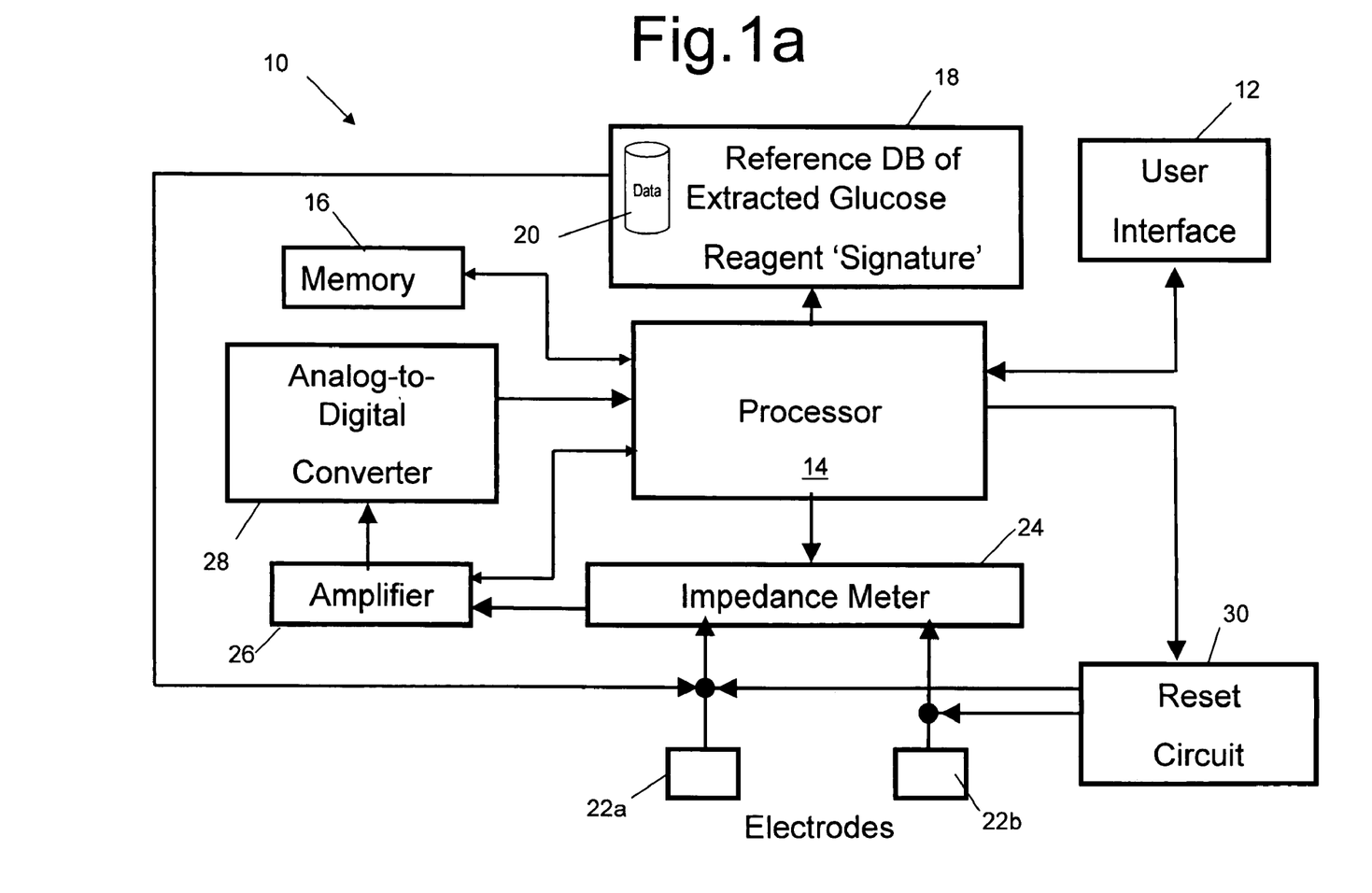
FIG. 1a is a schematic diagram illustrating one embodiment of the present invention.

Turning now to FIG. 1a, there is illustrated one aspect of the present invention. In this aspect, there is a measuring device 10 for measuring the levels of a substance in a living organism. The measuring device 10 comprises a user interface 12. The user interface 12 may comprise one or more interfaces which are capable of receiving input and presenting output to a user or software agent. Specific aspects of the user interface 12 may include a display, a touch sensitive input screen, input keys, microphones and/or speakers (not shown).

The user interface 12 may be in communication with a processor 14. In certain aspects of the present invention, the processor 14 controls the processes and various functions of the measuring device 10. In some aspects of the present invention, the processor 14 may be coupled to a first memory 16. The memory 16 may be built into the processor 14 or be an external memory chip. In certain aspects of the present invention, the processor 14 may also be in communication with a second memory 18. The second memory 18 may be an external memory chip or memory built into the processor 14. In certain embodiments, the second memory may contain a reference database 20, such as a database of extracted glucose reagent signatures.

In one embodiment, the reference database 20 may be a table of values correlating reference or signature frequencies to specific levels of a substance in a "reagent." As used in this application, a reagent is a substance typically mixed with a liquid or solvent to form a compound. The reagent may be selected because of its biological or chemical activity. As will be explained later, the reagent may be used to determine the self oscillating frequency of a substance. By using empirical techniques, a table of correlating the self oscillating frequencies to amounts of a substance in a reagent may be built and loaded into the database 20.

The memory 18 may be in communication with a pair of electrodes 22a and 22b. In certain embodiments, one electrode may be active-positive and the other electrode may be passive-negative. As will be explained later, the electrodes 22a and 22b are adapted to interact with the skin of the organism and may be used to measure the impedance between two points on the skin. In certain embodiments, the electrodes are in communication with an impedance meter 24 which determines or measures the impedance between the electrodes 22a and 22b. The impedance meter 24 may be in communication with an amplifier 26, which amplifies signals sent from the impedance meter 24.

In the illustrative embodiment, the amplifier 26 may in communication with an analog-to-digital converter 28 which converts analog signals from the amplifier to the digital signals. In some embodiments, the digital signals may be sent to the processor 14.

A reset circuit 30 may also be coupled to the measuring device 10 and in communication with the processor 14. The reset circuit 30 may also in communication with the electrodes 22a and 22b. In some embodiments, the reset circuit 30 may be adapted to clear or "short out" any residual charge between the electrodes. In other words, the reset circuit 30 clears any residual capacitance and/or changes polarization which may have developed on the skin between the electrodes. The measuring device 10 may be powered by a power source, such as a battery (not shown).

Figure 1B:
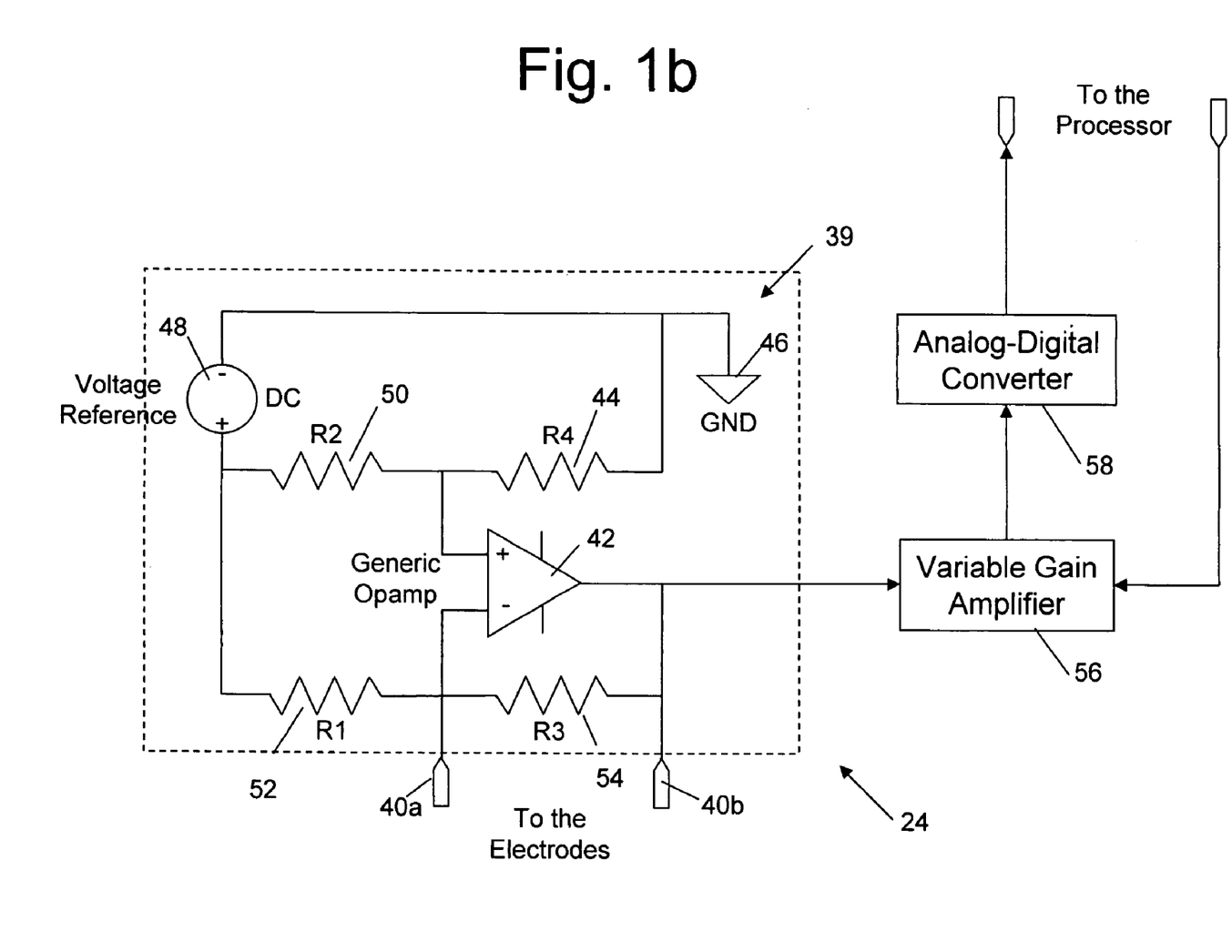
FIG. 1b is a schematic diagram illustrating an impedance meter which could be used in various embodiments of the present invention.

Turning now to FIG. 1b, there is illustrated one embodiment of the impedance meter 24. In this embodiment, a circuit 39 determines the relative change of impedance between two electrodes outputs a corresponding voltage which represents the change in impedance. In this embodiment, the circuit 39 may comprise leads 40a and 40b to the electrodes 22a and 22b (FIG. 1), respectively. The lead 40a may be coupled to the negative or inverting input of an operational amplifier 42. The positive or non-inverting input of the operational amplifier 42 may be coupled to a partial circuit comprising a resister 44, a common ground 46, a voltage reference 48, and a resistor 50. The positive lead of the voltage reference 48 and the negative lead of the resistor 50 may be coupled to a resistor 52. The resistor 52 may be coupled to the lead 40a and the negative input of the operational amplifier 42.

In this illustrative embodiment, the lead 40b is coupled to the output of the operational amplifier 42. A resistor 54 also couples the leads 40a to the lead 40b. The output of the operational amplifier 42 sends a voltage to a variable gain amplifier 56, which is also adapted to receive signals from the processor 14 (FIG. 1). Thus, the circuit 39 sends a voltage to the variable gain amplifier 56 which corresponds to the change in impedance between the electrodes. The variable gain amplifier 56 amplifies the voltage and sends the amplified signal to an analog-to-digital converter 58. In the illustrative embodiment, the analog-to-digital converter 58 converts the analog signals from the variable gain amplifier 56 and sends the converted digital signals to the processor 14.

Figure 1C:
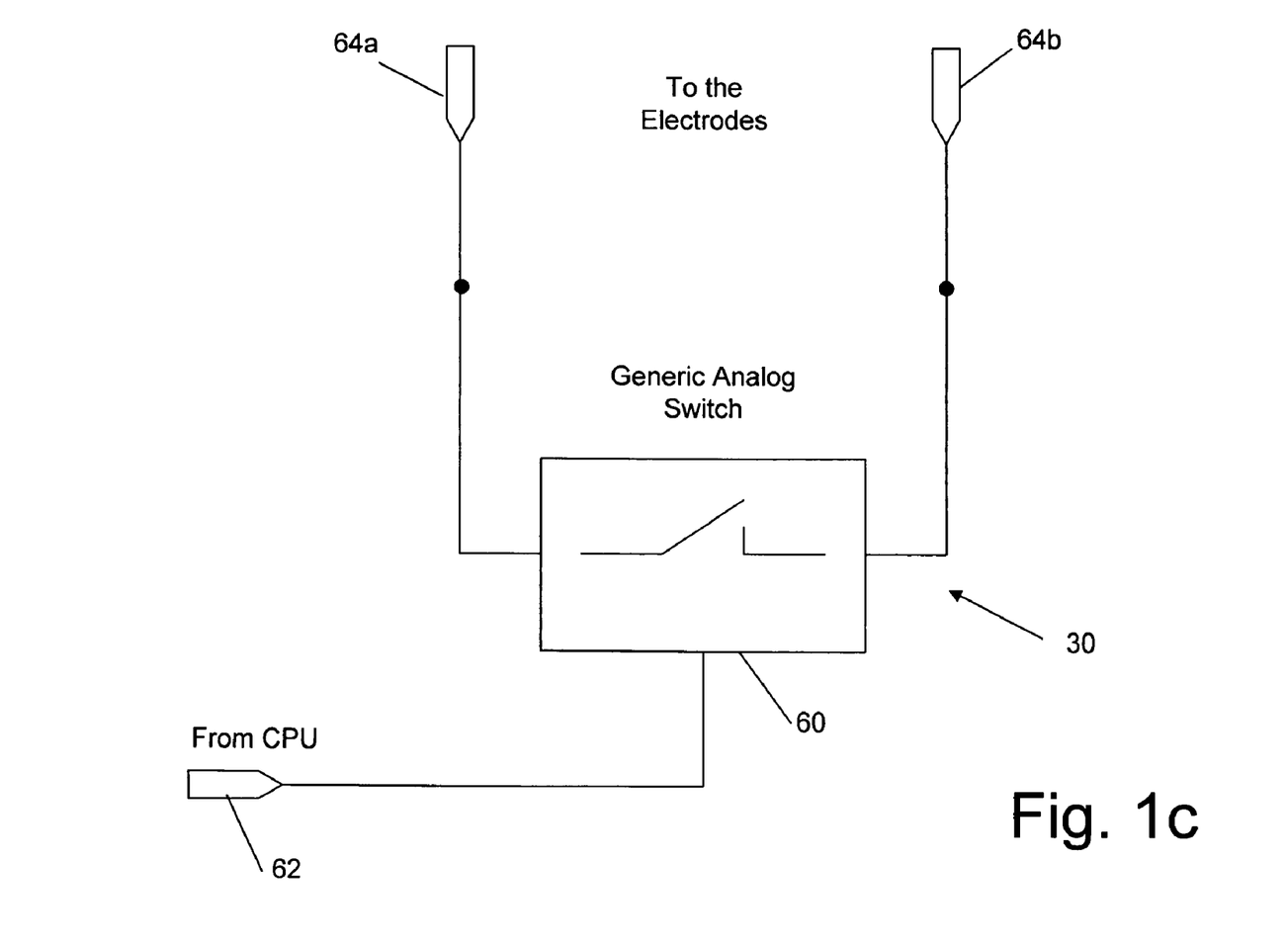
FIG. 1c is a schematic diagram illustrating a reset circuit which could be used in various embodiments of the present invention.

Turning now to FIG. 1c, there is illustrated one aspect of the reset circuit 30. In this illustrative embodiment, there is a generic analog switch 60 adapted to receive input commands from the processor 14 (FIG. 1) from a lead 62. The analog switch 60 may also be in communication with the electrodes 22a and 22b (FIG. 1) through the leads 64a and 64b, respectively. Upon receiving the appropriate command from the processor 14, the analog switch 60 is thrown, which effectively "shorts" out any residual charge between the electrodes. In other embodiments (not shown), the circuit may be adapted to alternate the polarity of the electrodes 22a and 22b.

Figure 2:
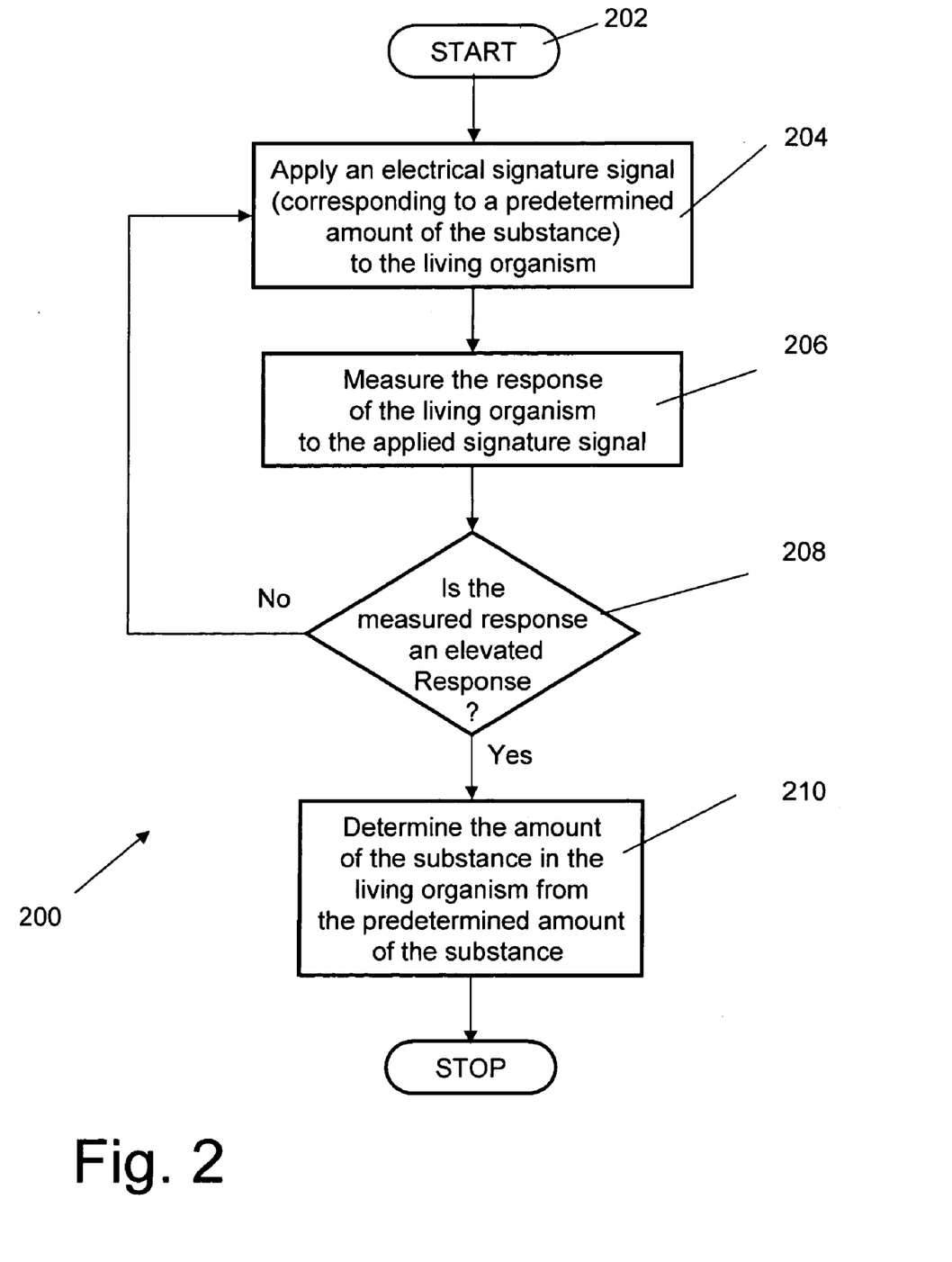
FIG. 2 illustrates a general process for non-invasively measuring quantitative information of substances in living organisms.

FIG. 2 illustrates a general method 200 to determine the amount of a particular substance in an organism, such as a human body. The process starts at step 202 and proceeds to step 204 where an electrical signature wave or signal corresponding to one frequency is applied to the electrodes (e.g., electrodes 22a and 22b of FIG. 1) which may be in contact with the skin of the organism. The applied electrical signature signal correlates to a predetermined concentration of the substance. In some aspects of the method, there is a pre-existing reference database (e.g., database 20 of FIG. 1) stored on a conventional memory chip containing correlations between "signature" signal frequencies (e.g., 22-44 kilohertz) and known concentrations of a substance reagent. Thus, each signature frequency in the database correlates to a known concentration of a substance in an organism.

In step 206, a response or "excitation" to the applied signature signal is measured. In step 208, the process determines whether the response is "elevated." In other words, did the organism respond in such a way as to indicate a positive correlation between applied electrical signal and the known concentration of the substance. If it is determined that the response to the applied electrical signature is elevated, then the process flows to step 210 where a correlation may be made between to determine the level of the substance (such as glucose) in the organism. On the other hand, if there is not an elevated response, the process may flow back to step 204, where, in some embodiments, a new electrical signature wave may be applied.

As will be explained below, in some embodiments, the process may iteratively apply a plurality of electrical signature signals, where each signal corresponds to a particular concentration of a substance. The electrical signature signal (or signals) that caused the greatest amount of excitation may be determined and the reference database may be again accessed to determine the particular level of the substance that corresponds with the frequency. The level of the substance can, therefore, be determined and displayed through a user interface.

As an example, the self-oscillation frequencies of different concentrations of glucose molecules in the human blood can be matched with similar frequencies of pre-known concentrations of glucose in reference solutions. Once a frequency is matched, the corresponding glucose level in the blood can be readily determined.

Figure 3A:
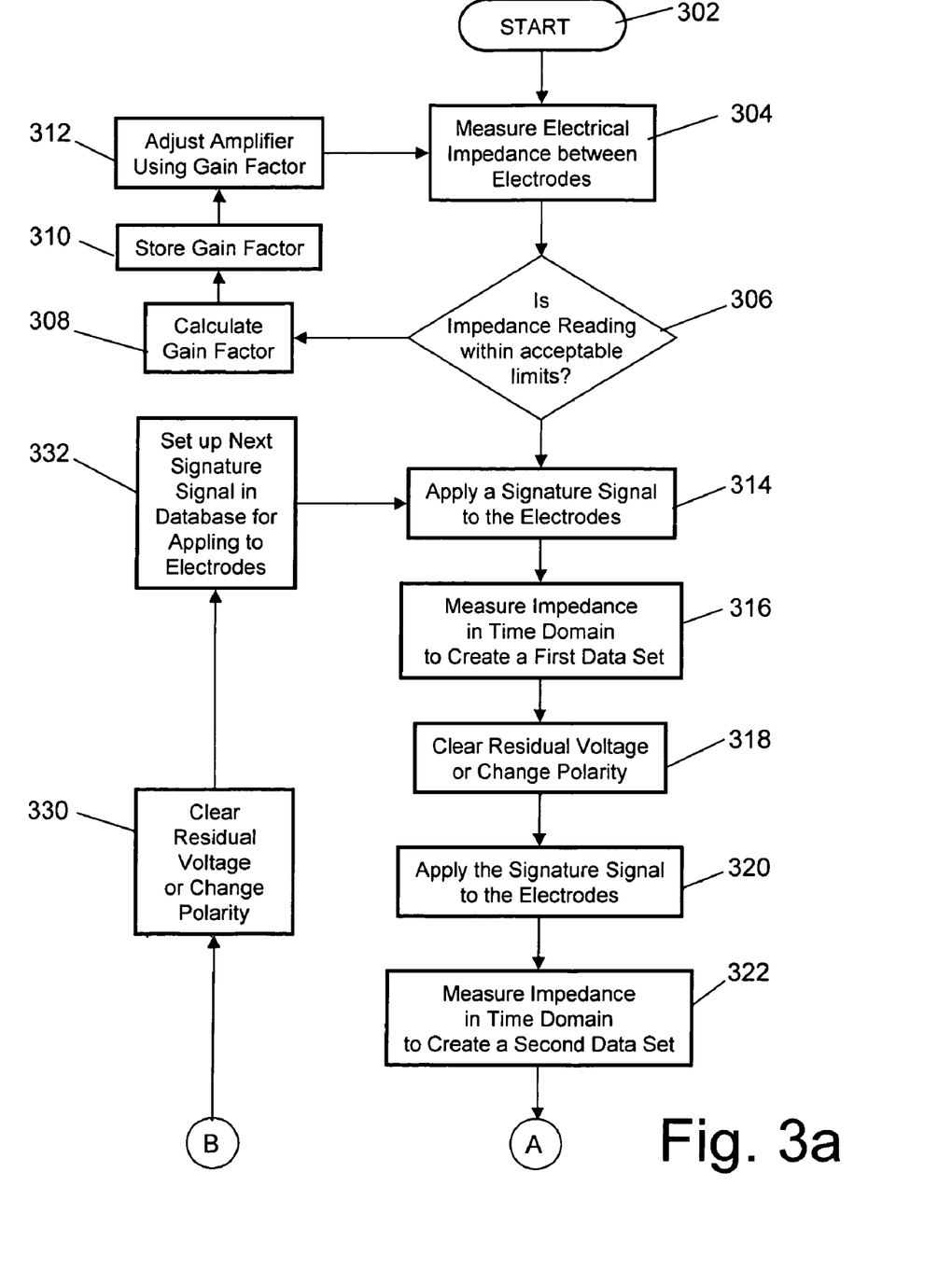
FIG. 3a illustrates a detailed process for non-invasively measuring quantitative information of substances in living organisms.
Figure 3B:
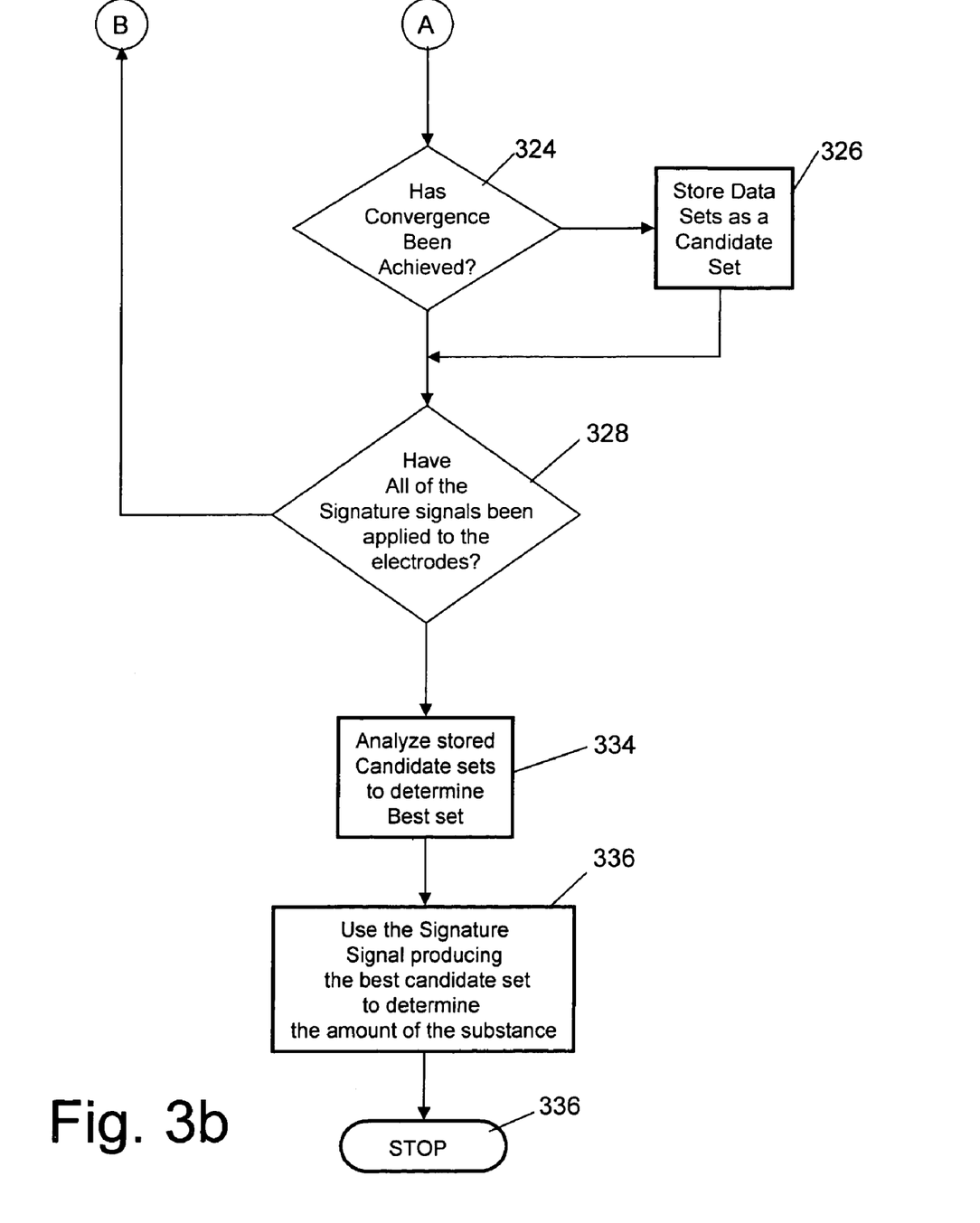

FIGS. 3a and 3b illustrate a detailed exemplary embodiment of the general method illustrated in FIG. 2. The process starts in step 302. In certain embodiments, a signal from the user interface initiates the process. In other aspects, the process may be initiated by the processor as a result of a preprogrammed schedule or timer circuit. After initiation, the process then proceeds to step 304 where the electrical impedance between two different points on the skin is measured via the electrodes 22a and 22b. In certain embodiments, the two points may be acupuncture points which lie on different meridians. At step 306, the process determines whether the impedance signal (e.g., the voltage representing the impedance) is within acceptable predetermined limits. For instance, if the readings from the impedance measurement is too low, the amplifier gain may be adjusted. If the readings are not within the predetermined limits, in step 308, a gain factor is calculated. In step 310, the gain factor may be stored in memory for later use in making additional impedance measurements. In step 312, the gain factor may be used to adjust the gain of the amplifier. The process then flows back to step 304 where the impedance is again measured. At step 306, the process determines whether the new impedance signal is within acceptable predetermined limits. Once it has been determined the signal is within acceptable limits, process flows to step 314.

Figure 4A:
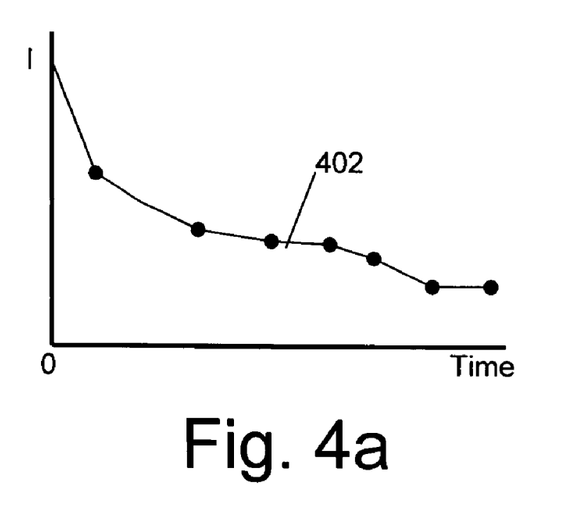
FIGS. 4a-4c illustrate graphs of curves which illustrate impedance measurements occurring in the time domain.

In step 314, a first signature signal from the reference database 20 is applied on the electrodes. In some embodiments, the signature wave corresponds to a known level of glucose. In step 316, a series of measurements of the electrical impedance is then performed in the time domain which creates a first data set. The first data set may be represented by a curve 402 on the graph illustrated in FIG. 4a. In FIG. 4a, the vertical axis represents the response or measured impedance. The horizontal axis represents time. Thus, the curve 402 represents the impedance response over time resulting from the application of the signature signal which is applied at time=0. In other words, each point on the curve represents the measured value of impedance at a particular time from the occurrence of the application of the signature signal.

Figure 4B:
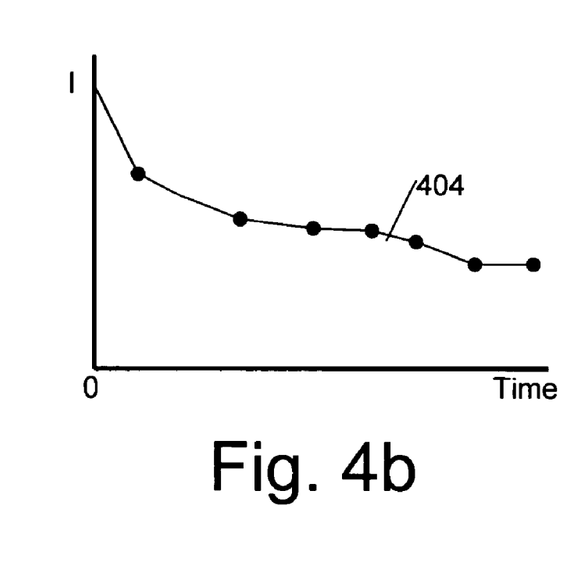

Turning back to FIG. 3, in step 318, the residual voltage on the electrodes may then be cleared as discussed in reference to FIG. 1c. In step 320, the signature signal is again applied through the electrodes. This is the same signal which was applied in step 314. In step 322, another series of measures of the electrical impedance is performed in the time domain which creates a second data set. The second data set may be represented by curve 404 of the graph illustrated in FIG. 4b. In certain embodiments, the steps 314 through 322 may be repeated to produce additional data sets if predefined indicators, such as quality-of-measurement indicators, are not met.

Figure 4C:
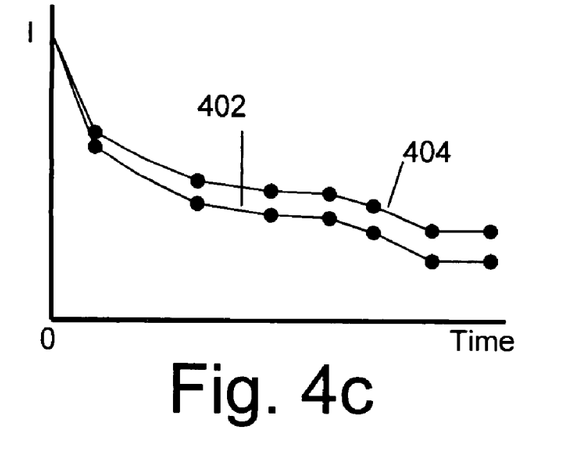

In step 324, the data sets are compared to each other to determine whether convergence has been achieved. The amount of convergence may be graphically represented by the graph illustrated in FIG. 4c which shows curve 402 superimposed onto curve 404. If convergence has not been achieved, the process flows directly to step 328. If convergence has been achieved, then in step 326, the process stores the signature sets as a candidate data set before it flows to step 328.

In step 328, the process determines whether all of the signature signals in the database have been applied. If not, the process flows to step 330 (FIG. 3a), where the residual voltage is removed as discussed in reference to FIG. 1c. From step 330, the process flows to step 332, where the next signature signal in the database is set up to be applied to the electrodes. The process then flows back to step 314, where the steps 314 through 328 are repeated for the new signature signal. On the other hand, if in step 328, it is determined that all of the signature signals have been applied to the electrodes, the process flows to step 334.

In step 334, the logic reviews the stored candidate data sets to determine the set having the maximum convergence or the "best" candidate out of the stored candidate data sets. Using the frequency responsible for producing the best candidate, in step 336, the reference database may then be accessed to determine the level of the substance that corresponds with the signal. The level of the substance can, therefore, be determined and sent to a user interface. The process ends at step 338.

Figure 5:
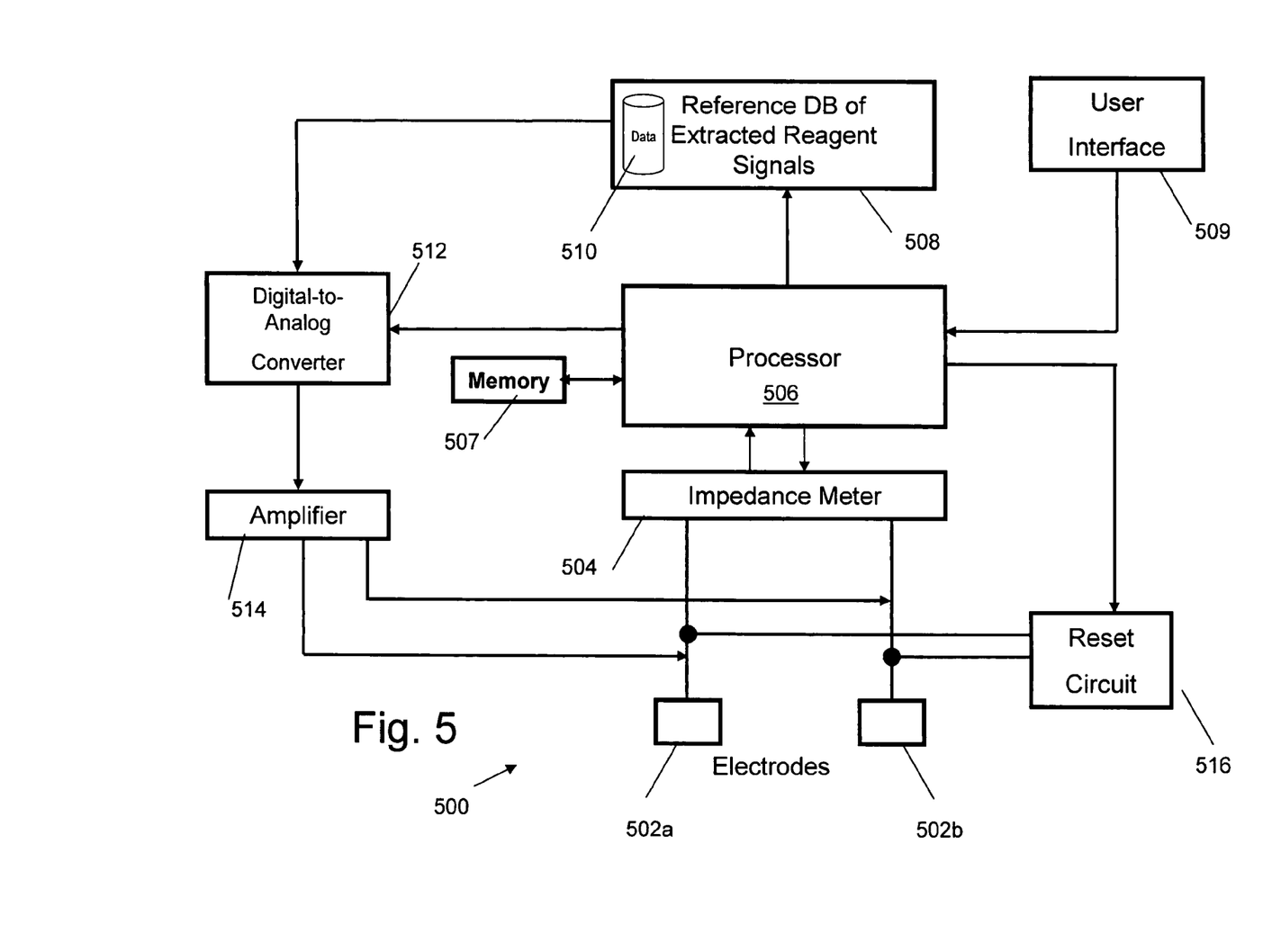
FIG. 5 is a schematic diagram illustrating another embodiment of the present invention.

Turning now to FIG. 5, there is an alternative measuring device 500 for measuring the levels of a substance in a living organism. The measuring device 500 comprises a pair of electrodes 502a and 502b. One electrode is active-positive and the other electrode is passive-negative. The electrodes 502a and 502b are adapted to interact with the skin of the organism and may measure the electro conductivity between two points on the skin, such as two points on different meridians. The electrodes are in communication with an impedance meter 504 that measures the impedance between the electrodes 502a and 502b. The impedance meter 504 may be in communication with a processor 506. As will be explained in detail below, the processor 506 controls various aspects of the device 500. The processor 506 is in communication with a first memory device 508 for storing a reference database 510. In some embodiments, the first memory device may be a conventional memory chip. In other embodiments, the processor 506 may be in communication with a second memory device 507 for the storage of temporary variables and measured data. The second memory device 507 may be either built into the processor or as an external chip. The processor 506 may also be in communication with a user interface 509, which may take a variety of embodiments, such as a screen and input device.

In some embodiments, the processor 506 may also be in communication with a digital-to-analog converter 512 which converts digital signals from the processor to the analog signals. In some embodiments, the analog signals may be sent to an amplifier 514 which is adapted to send signals to the electrodes 502a and 502b. A reset signal generator 516 is also in communication with the electrodes 502a and 502b and is adapted to send signals to the electrodes. The signal generator 516 may also be in communication with the processor 506. In certain embodiments, the signal generator 516 is adapted to alternate polarity of the signal to electrodes and the amplifier 514. In other embodiments, the signal generator may be a reset circuit similar to the reset circuit 30 discussed in reference to FIG. 1a.

As in the embodiment discussed in reference to FIG. 1a, the user interface 509 may send a signal to the processor 106 to initiate a process. In response, the processor 506 initiates a process which causes the impedance meter 504 to read the impedance between the electrodes 502a and 502b. The impedance meter 504, amplifies the impedance signal, digitizes the impedance signal and sends it back to the processor 506. The processor uses the initial impedance reading to calculate a gain factor which may be stored in the memory 507 for later use.

The processor 506 then initiates a process which reads the database 510 stored in the memory 508. The codes or signature signals from the database 510 are then sent to the digital-to-analog converter 512, which converts the digital signals to analog signals. The analog signals may then sent to the amplifier 514, which amplifies the analog signal and sends the signals to the electrodes 502a and 502b. The impedance between the electrodes 502a and 502b may then be read by the impedance meter 504. The substance amount in the organism may then be determined according to the iterative processes similar to those discussed above.

Figure 6A:
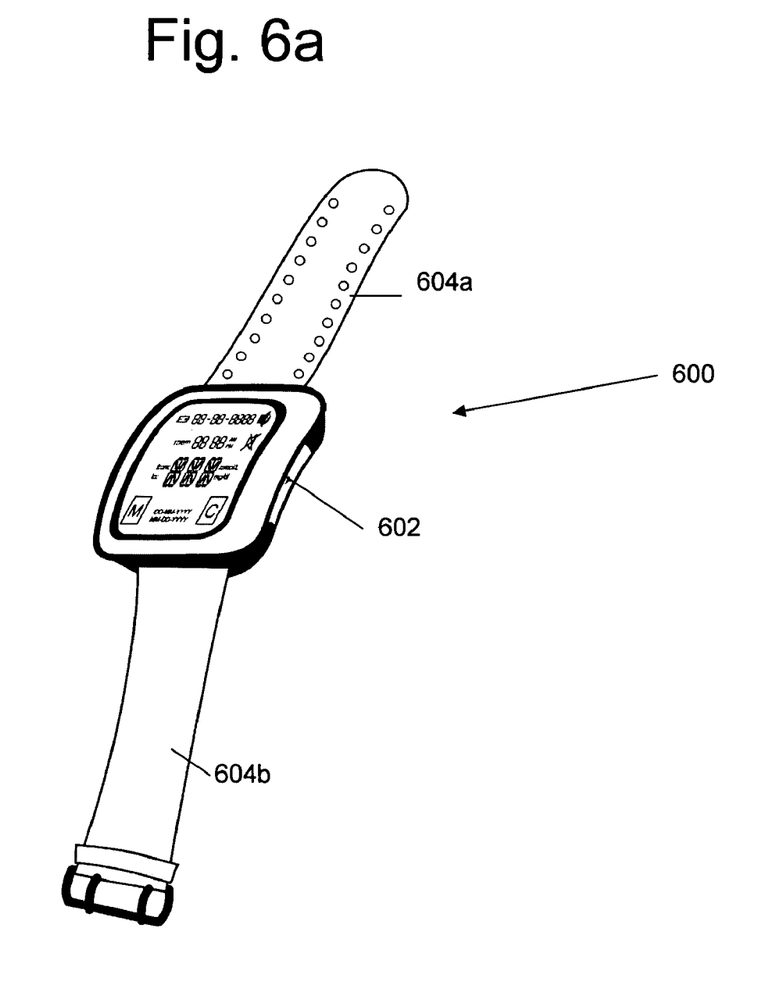
FIG. 6a is a perspective view illustrating a portable device incorporating one or more aspects of the present invention.

FIG. 6a illustrates an example embodiment of a system 600 which is designed to be worn on a person's wrist. As illustrated, there is a portable measurement device 602 which is adapted to be coupled to wrist bands 604a and 604b. The measurement device 602 may contain all of the components discussed previously in reference to FIGS. 1a through 1c or FIG. 5.

Figure 6B:
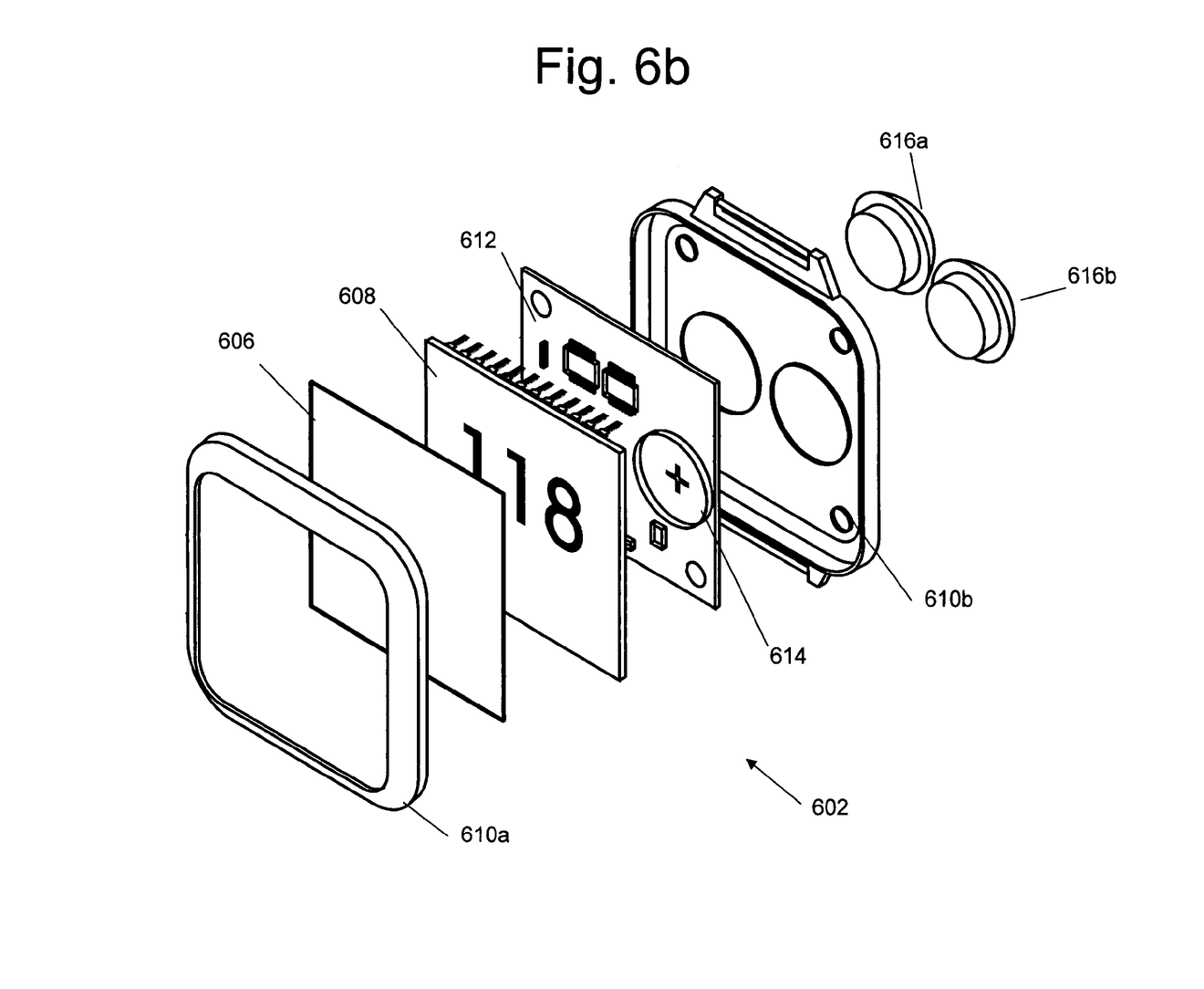

FIG. 6b is an exploded perspective view of the portable device 602 illustrated in FIG. 6a. In this embodiment, the measurement device 602 includes a user interface which comprises a touch screen 606 and a liquid crystal display (LCD) 608. The touch screen 606 accepts input from a user and the LCD 608 displays information and the results of processing. In this example embodiment, there are housing members 610a and 610b which encloses the various components, such as the processor and memory devices previously discussed. In this embodiment, the components may be assembled on a printed circuit board 612. In this particular example, a power source, such as a lithium battery 614 provides the device with the necessary power. Electrodes 616a and 616b may be located on underside of watch and are adapted to touch the back side of a human wrist. In certain embodiments, the electrodes 616a and 616b are made from a conductive material, such as copper, gold, silver, metal, stainless steel or any combination thereof. In the illustrated embodiment, the electrodes 616a and 616b may be spaced to line up over acupuncture points of endocrine or lymphatic system meridian.

The foregoing description of the embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto.

For instance, in some embodiments, there is method of determining a substance in a living organism, the method comprising: applying an electrical signature signal to the living organism, wherein the electrical signature signal corresponds to a predetermined amount of the substance; measuring the response of the living organism to the applied signature signal; and determining whether an elevated response has resulted from applying the electrical signature, if so, then determining the amount of the substance in the living organism from the predetermined amount of the substance.

There may also be a method similar to that described above, further comprising providing a plurality of electrical signal signals, wherein each signature signal in the plurality of signature signals corresponds to a different predetermined amount of the substance.

There may also be a method similar to that described above, wherein the plurality of signature signals correspond to a predetermined amount of the substance ranging from a low amount of the substance to a high amount of the substance.

There may also be a method similar to that described above, wherein the method of claim 1 is repeated for each electrical signature signal in the plurality of electrical signature signals.

There may also be a method similar to that described above, wherein the substance is glucose.

There may also be a method similar to that described above, wherein the measuring the response comprises measuring the impedance between two different points on the skin of the living organism.

There may also be a method similar to that described above, wherein the measuring the response comprises: measuring a plurality of impedance values over time resulting from applying the signature signal corresponding to a predetermined amount of the substance to establish a first data set of measure data values; reapplying the electrical signature signal to the living organism; measuring a plurality of impedance values over time resulting from applying the signature signal to establish a second data set of measure data values.

There may also be a method similar to that described above, further comprising clearing any residual charges between the points on the skin.

There may also be a method similar to that described above, wherein the determining comprises: determining whether there is convergence between the first and second data sets; if there is convergence between the first and second data sets, then storing the data sets as a candidate set.

There may also be a method similar to that described above, further comprising: examining each stored candidate set to determine the candidate set having the largest convergence, and setting the amount of the substance to be the signature that corresponds to the candidate set having the largest convergence.

In other embodiments, there may be an apparatus for measuring a substance in a living organism, the apparatus characterized by: a processor means; at least two electrode means for applying and receiving signals, an impedance measuring means for determining the impedance between the at least two electrode means; a memory means for storing a database of electrical signature signals, wherein each electrical signature signal corresponds to different amounts of a substance; and a means for applying the electrical signature signals to the at least two electrode means.

There may also be an apparatus similar to that described above, further characterized by an amplifier means for amplifying signals from the impedance determining means; and an analog-to-digital conversion m eans for converting analog signals from the amplifier means to digital signals.

There may also be an apparatus similar to that described above, further characterized by a gain adjusting means for adjusting the gain of the amplification means.

There may also be an apparatus similar to that described above, further characterized by a memory means for storing a gain factor determined from the gain adjusting means.

There may also be an apparatus similar to that described above, further characterized by a reset means for discharging any residual voltage between the at least two electrode means.

There may also be an apparatus similar to that described above, further characterized by a housing means for housing components of the measuring apparatus, wherein the housing means is adapted for engagement with a strap means.

There may also be an apparatus similar to that described above, wherein the strap means is a wrist strap means.

There may also be an apparatus similar to that described above, wherein the electrode means are made in part from stainless steel.

There may also be an apparatus similar to that described above, wherein the substance is glucose.

There may also be an apparatus similar to that described above, further characterized by: an digital-to-analog conversion means for converting digital signals from the memory means; and an amplifier means for amplifying analog signals from the digital-to-analog conversion means.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

The invention claimed is:

1. A method for determining the amount of glucose in a human body, the method comprising:
    (a) providing a plurality of electrical signature signals, wherein each electrical signature signal corresponds to a predetermined indicator of glucose;
    (b) applying an electrical signature signal from the plurality of electrical signals to at least two electrodes;
    (c) measure a first change in impedance over time resulting from the application of the electrical signature signal to produce a first set of measured data;
    (d) applying the electrical signature signal from the plurality of electrical signals to the two electrodes;
    (e) measure a second change in impedance over time resulting from the application of the second electrical signature signal to produce a second set of measured data;
    (f) determining whether the first set of measure data and the second set of measured data have converged, if yes, then storing the first set and second set as a candidate data set;
    (g) determining whether all of the electrical signature signals in the plurality of electrical signature signals have been applied,
        if no, then selecting a new electrical signature signal and repeating steps (b) through (g);
        if yes, then: selecting the candidate set having a maximum level of convergence, and determining the amount of substance from the electrical signature signal producing the selected candidate set.

2. The method of claim 1, farther comprising:
    measuring the electrical impedance between the electrodes to obtain a signal indicating the electrical impedance,
    amplifying the signal indicating the electrical impedance,
    determining whether the amplified signal is within a predetermined criteria, if not, then:
        calculating a gain factor,
        adjusting an amplifier using the gain factor; and
        re-measuring the electrical impedance between the electrodes to obtain a signal indicating the electrical impedance.

3. The method of claim 1 further comprising clearing residual voltage between the at least two electrodes.

4. A method of determining a substance in a living organism, the method comprising:
    (a) providing a plurality of electrical signature signals, wherein each electrical signature signal corresponds to a predetermined indicator of the substance;
    (b) applying an electrical signature signal from the plurality of electrical signals to at least two electrodes;
    (c) measure a first change in impedance over time resulting from the application of the electrical signature signal to produce a first set of measured data;
    (d) applying the electrical signature signal from the plurality of electrical signals to the two electrodes;
    (e) measure a second change in impedance over time resulting from the application of the second electrical signature signal to produce a second set of measured data;
    (f) determining whether the first set of measure data and the second set of measured data have converged, if yes, then storing the first set and second set as a candidate data set;
    (g) determining whether all of the electrical signature signals in the plurality of electrical signature signals have been applied, if no, then selecting a new electrical signature signal and repeating steps (b) through (g);
    if yes, then:
        selecting the candidate set having a maximum level of convergence, and
        determining the amount of substance from the electrical signature signal producing the selected candidate set.

5. The method of claim 4, further comprising:
    measuring the electrical impedance between the electrodes to obtain a signal indicating the electrical impedance,
    amplifying the signal indicating the electrical impedance,
    determining whether the amplified signal is within a predetermined criteria, if not, then:
        calculating a gain factor,
        adjusting an amplifier using the gain factor; and
        re-measuring the electrical impedance between the electrodes to obtain a signal indicating the electrical impedance.

6. The method of claim 4 further comprising clearing residual voltage between the at least two electrodes.

* * * * *